United States Patent [19]

Kandathil

[11] Patent Number: 4,711,739

[45] Date of Patent: Dec. 8, 1987

[54] ENZYME PRESPOTTER COMPOSITION STABILIZED WITH WATER INSOLUBLE POLYESTER OR POLYETHER POLYOL

[75] Inventor: Thomas V. Kandathil, Racine County, Wis.

[73] Assignee: S. C. Johnson & Son, Inc., Racine, Wis.

[21] Appl. No.: 943,226

[22] Filed: Dec. 18, 1986

[51] Int. Cl.$^4$ .......................... C11D 3/20; C11D 3/37; C11D 3/386; C12N 9/96

[52] U.S. Cl. .................................... 252/139; 252/89.1; 252/153; 252/170; 252/171; 252/173; 252/174.12; 252/174.19; 252/174.21; 252/174.22; 252/174.23; 252/546; 252/DIG. 2; 252/DIG. 12; 252/DIG. 14; 252/DIG. 19; 435/188

[58] Field of Search ....................... 252/174.21, 174.23, 252/174.12, DIG. 12, 139, 89.1; 435/188

[56] References Cited

U.S. PATENT DOCUMENTS

| | | | |
|---|---|---|---|
| 2,642,376 | 6/1955 | Gale | 195/63 |
| 3,557,002 | 1/1971 | McCarty | 252/89 |
| 3,575,864 | 4/1971 | Innerfield | 252/89 |
| 3,600,319 | 8/1971 | Gedge | 252/114 |
| 3,607,653 | 9/1971 | Ziffer | 195/63 R |
| 3,627,688 | 12/1971 | McCarty | 252/153 |
| 3,634,258 | 1/1972 | Wildi | 252/89 |
| 3,634,266 | 1/1972 | Thelle | 252/132 |
| 3,635,828 | 1/1972 | Benjamin | 252/99 |
| 3,655,570 | 4/1972 | Isono | 252/132 |
| 3,676,374 | 7/1972 | Zaki | 252/551 |
| 3,682,284 | 8/1972 | Innerfield | 252/539 |
| 3,697,451 | 10/1972 | Mausner | 252/545 |
| 3,707,504 | 12/1972 | Johnson | 252/135 |
| 3,707,505 | 12/1972 | Maeda | 252/136 |
| 3,723,327 | 3/1973 | van Kampen | 252/110 |
| 3,741,902 | 6/1973 | Barrett, Jr. | 252/90 |
| 3,746,649 | 7/1973 | Barrett, Jr. | 252/170 |
| 3,749,671 | 7/1973 | Gedge | 252/89 |
| 3,755,085 | 8/1973 | Tivin | 195/68 |
| 3,761,420 | 9/1973 | Bogardus | 252/171 |
| 3,781,212 | 12/1973 | Smillie | 252/89 |
| 3,819,528 | 6/1974 | Berry | 252/153 |
| 3,943,063 | 3/1976 | Morishita | 252/316 |
| 3,953,353 | 4/1976 | Barrett, Jr. | 252/174 |
| 4,009,076 | 2/1977 | Green | 195/63 |
| 4,011,169 | 3/1977 | Diehl | 252/95 |
| 4,090,973 | 5/1978 | Maguire, Jr. | 252/89 R |
| 4,111,855 | 9/1978 | Barrat | 252/545 |
| 4,142,999 | 3/1979 | Bloching | 252/544 |
| 4,169,817 | 10/1979 | Weber | 252/545 |
| 4,176,079 | 11/1979 | Guerry | 252/90 |
| 4,238,345 | 12/1980 | Guilbert | 252/174.12 |
| 4,243,543 | 1/1981 | Guilbert | 252/105 |
| 4,272,396 | 6/1981 | Fukano | 252/174.12 |
| 4,326,985 | 4/1982 | Blair, Jr. | 252/358 |
| 4,404,115 | 9/1983 | Tai | 252/135 |
| 4,438,009 | 3/1984 | Brusky et al. | 252/90 |
| 4,462,922 | 7/1984 | Boskamp | 252/174.12 |
| 4,511,488 | 4/1985 | Matta | 252/162 |
| 4,561,998 | 12/1985 | Wertz et al. | 252/547 |
| 4,594,184 | 6/1986 | Cook et al. | 252/542 |

*Primary Examiner*—Paul Lieberman

[57] ABSTRACT

The present invention relates to water-in-oil emulsion prespotter laundry compositions. More particularly, the invention relates to water-in-oil emulsion prespotter laundry compositions containing enzymes and specific polyester or polyether polyols, which immobilize the enzymes to prevent their degradation during prolonged storage.

14 Claims, No Drawings

ENZYME PRESPOTTER COMPOSITION STABILIZED WITH WATER INSOLUBLE POLYESTER OR POLYETHER POLYOL

BACKGROUND OF THE INVENTION

The present invention relates to water-in-oil emulsion prespotter laundry compositions. More particularly, the invention relates to water-in-oil emulsion prespotter laundry compositions containing enzymes and specific polyester or polyether polyols, which stabilize the enzymes to prevent their degradation during prolonged storage.

The use of detergent and laundry prespotter compositions containing enzymes is well known in the art. For detergent compositions containing enzymes, see, for example, U.S. Pat. Nos. 3,557,002; 3,634,258; 4,090,973; 4,238,345; and 4,272,396. For prespotter compositions containing enzymes, see, for example, U.S. Pat. Nos. 3,741,902 and 3,953,353.

Moreover, the art recognizes "that the formulation of enzyme-containing liquid detergent compositions is a very delicate task due to the rapid decrease of the enzymatic activity in aqueous medium during storage."(U.S. Pat. No. 4,111,855, col. 1, lines 39–42).

Numerous attempts have been made to provide aqueous enzyme-containing compositions, wherein the enzymatic activity is claimed to be preserved by the incorporation of stabilizing agents. For example, the following enzyme stabilizing agents are disclosed in the patent literature. U.S. Pat. No. 3,557,002 (a short chain alkyl monohydroxy alcohol or an alkoxy short chain monohydroxy alcohol, along with a nonionic or zwitterionic detergent): U.S. Pat. No. 3,607,653 (polyethylene glycol polymers); U.S. Pat. No. 3,627,688 (dialkyl glycol ethers, heterocylic ethers and dialkyl ketones, along with a nonionic or zwitterionic detergent); U.S. Pat. No. 3,682,842 (enzyme-ion binding agents such as trichloracetic acid, tungstic acid, phosphotungstic acid, tannic acid, sulfosalicyclic acid, and certain dyes such as methylene blue, saffronin and inuline scarlet); U.S. Pat. No. 3,761,420 (polyhydric alcohols having 2 to 6 carbons and from 2 to 6 hydroxyl groups per molecule, and a chelating agent); U.S. Pat. No. 3,781,212 (colloidal silica and/or dissolved carbon dioxide); U.S. Pat. No. 3,819,528 (calcium ion and an organic compound selected from the group consisting of aliphatic glycols and 1,3-propane diols); U.S. Pat. No. 4,111,855 (a polyacid capable of forming water-soluble calcium-complexes); U.S. Pat. No. 4,142,999 (mono- and polyvalent alcohols and ethers thereof, and an alkoxylated alkylamine); U.S. Pat. No. 4,169,817 (water soluble hydroxy alcohols selected from glycerol, alkylene glycols in which the alkylene group contains from 2 to 8 carbon atoms, such as ethylene glycol, propylene glycol, butylene glycol, hexylene glycol, and sorbitol); U.S. Pat. No. 4,238,345 (an antioxidant and a hydrophilic polyol, which optimizes the preservative or stabilizing effect of the antioxidant); U.S. Pat. No. 4,404,115 (an alkali metal pentaborate, optionally with an alkali metal sulfite and/or a polyol): U.S. Pat. No. 4,462,922 (a mixture of boric acid or an alkali metal borate with a polyol or a polyfunctional amino compound, together with a certain level of a reducing alkali metal salt such as sodium sulfite); and U.S. Pat. No. 4,243,543 (an antioxidant and a hydrophilic polyol having a molecular weight less than about 500).

These numerous attempts to stabilize enzymes in aqueous compositions show the critical need for such compositions. None of these compositions, however, disclose the water-in-oil emulsion prespotter composition of the present invention.

Water-in-oil emulsion prespotter compositions without enzymes and polyether polyols or polyester polyols are disclosed in U.S. Pat. No. 4,438,009.

It has now been surprisingly found that enzyme degradation can be substantially avoided by formulating enzyme-containing water-in-oil emulsion prespotter laundry compositions comprising at least one of a polyester polyol having a hydroxyl number between about 28 and 690 or a polyether polyol having a hydroxyl number between about 28 and 690.

It has also been surprisingly found that enzyme-containing water-in-oil emulsion prespotter laundry compositions of this invention exhibit superior stain removal.

It is an object of this invention to provide stable enzyme-containing water-in-oil emulsion prespotter laundry compositions which retain an effective enzyme activity under prolonged storage conditions.

It is another object of this invention to provide stable enzyme-containing water-in-oil emulsion prespotter laundry compositions which exhibit excellent cleaning and stain removal properties.

These and other objects can be readily observed from the following disclosure.

SUMMARY OF THE INVENTION

The present invention relates to an improved water-in-oil prespotter laundry composition comprising: (a) from about 0.1 to 1% by weight of at least one enzyme; (b) from about 5 to 30% by weight of at least one ethoxylated nonionic surfactant: (c) from about 0.2 to 5% by weight of at least one of a water insoluble polyester polyol having a hydroxyl number of about 28 to 690 or a water insoluble polyether polyol having a hydroxyl number from about 28 to 690; (d) from about 0.1 to 10% by weight of at least one builder salt; (e) from about 5 to 70% by weight of at least one hydrocarbon solvent; and (f) the balance water; and the composition having a pH in the range from about 5 to 9.

The present invention is also concerned with the method of producing the above composition which comprises the steps of: (1) mixing (a) from about 0.1 to 1% by weight of at least one enzyme; (b) from about 5 to 30% by weight of at least one ethoxylated nonionic surfactant; (c) from about 0.2 to 5% by weight of at least one of a water insoluble polyester or a water insoluble polyether polyol; and (d) from about 5 to 70% by weight of at least one hydrocarbon solvent; and (2) blending from about 0.1 to 10% by weight of at least one builder salt in an aqueous carrier; and (3) adding the mixture of (1) to the blend of (2).

DETAILED DESCRIPTION OF THE INVENTION

The enzymes utilized in accordance with the teachings of this invention include proteases, lipases, amylases, and mixtures thereof. These enzymes and their methods of preparation are fully disclosed in the patent literature. See, for example, U.S. Pat. Nos. 3,557,002, cols. 2 and 3; 3,627,688, col. 2; and 3,697,451, col. 2.

The amount of enzyme utilized is not critical, with the lower amount dictated by an amount sufficient to obtain adequate stain removal, and the upper limit by economics. Generally, from about 0.1 to 1% by weight is preferred. Unless otherwise indicated, all percentages of ingredients are calculated as weight percentages based on the total weight of the prespotter composition.

The enzymes, which are organic catalysts produced by living cells, degrade or break down soils and stains, which can then be removed by the detergent composition. By attacking and degrading stains and soils in this manner, the stains and soils are not available to act as binding agents for other soils, and the overall cleaning and washing process is thereby materially advanced.

Proteolytic enzymes break down protein-type stains caused by blood, eggs, infants' formula, grass and the like. Amylolytic enzymes are specific for starches and sugars as in the case of gravy, chocolate, ice cream and pudding stains. Lipolytic enzymes facilitate the removal of fat and grease stains caused by bacon grease, butter, cooking oils, body oils, and the like.

The ethoxylated nonionic surfactants used in accordance with the teachings of this invention are those generally known and used in detergent compositions. The ethoxylated nonionic surfactants include ethoxylated aliphatic alcohols, ethoxylated alkyl phenols, and mixtures thereof. More specifically, the ethoxylated nonionic surfactants include primary or secondary alcohol ethoxylates having a carbon length of 8 to 22 carbon atoms and containing from 1 to about 100 moles of ethylene oxide per mole of alcohol; alkylphenol ethoxylates containing from 1 to about 50 moles of ethylene oxide per mole of phenol, and mixtures thereof.

The ethoxylated nonionic surfactants are typically produced by the condensation reaction of one mole of a primary or secondary alcohol containing 8 to 22 carbon atoms with 1 to about 100 moles of ethylene oxide.

Examples of commercially available ethoxylated nonionic surfactants include the Neodol series from Shell, e.g., Neodol 23-6.5, having alcohols with carbon chains of 12–13 and an average of 6.5 moles of ethylene oxide per mole of alcohol; Neodol 25-7 (12–15 carbons, 7 moles ethylene oxide); Neodol 25-9 (12–15 carbons, 9 moles ethylene oxide); and Neodol 45-11 (14–15 carbons, 11 moles ethylene oxide).

Other commercial examples include the linear secondary alchols with carbon lengths from 11 to 15 with an average of 7 moles of ethylene oxide, such as Tergitol 15-S-7 and its counterpart. Tergitol 15-S-9, which has an average of 9 moles of ethylene oxide.

The alkyl phenol ethoxylates usually contain an alkyl group having between 6 and 18 carbons and an average of about 3 to 25 moles of ethylene oxide per mole of phenol. Specific examples include nonyl phenol polyglycol ethers with an average of 9.5 moles of ethylene oxide such as IGEPAL CO-630 from GAF; dodecyl phenol polyglycol ethers with an average of 12 moles of ethylene oxide; and octyl phenol polyglycol ethers with an average of 9 moles of ethylene oxide such as Triton X-100. For further examples, see U.S. Pat. No. 3,953,353, cols. 2–6.

The concentration of ethoxylated nonionic surfactant utilized in accordance with this invention is not critical. Generally, compositions containing between about 5 and 30% by weight of the total composition are preferred. More preferred concentrations are given in the examples herein. These ethoxylated nonionic surfactants are used as wetting agents and emulsifiers to allow the prespotter composition to wet and emulsify the stain to be removed.

The builder salts utilized in accordance with this invention include citrates, gluconates, borates, silicates, phosphates, chlorides, bicarbonates, carbonates, polyacetates, acetates, polyphosphates, phosphates, maleates, fumerates, formates, carboxylates, $C_2$ to $C_{10}$ dicarboxylates, and mixtures thereof.

Specific salts in the above classes which are particularly preferred include sodium citrate, sodium gluconate, borax, sodium silicate, sodium tripolyphosphate, sodium chloride, sodium sesquicarbonate, sodium carbonate, sodium pyrophosphate, potassium chloride, magnesium chloride, zinc ammonium citrate and mixtures thereof.

The most preferred salts are sodium citrate, borax, sodium silicate, sodium tripolyphosphate and sodium pyrophosphate. They do not cause corrosion problems in aerosol containers. For non-aerosol compositions, preferred salts include sodium citrate, potassium chloride, sodium chloride, magnesium chloride, and mixtures thereof.

The concentration of builder salt preferably utilized in accordance with this invention is from about 1 to 10 percent by weight of the composition. More preferred concentrations are given in the examples below.

Water is known to have a deteriorating effect on the catalytic activity of hydrolytic enzymes. During storage in water and in the absence of a substrate capable of being hydrolyzed, the enzymes tend to digest themselves.

To address the problem of enzyme instability, at least one of a water insoluble polyether polyol having a hydroxyl number from about 28 to 690 or a water insoluble polyester polyol having a hydroxyl number from about 28 to 690 is employed. With polyols having a hydroxyl number below about 28, it is extremely difficult to make a stable emulsion. With hydroxyl numbers above about 690, the polyol is extremely difficult to disperse.

The polyether polyols used in the practice of this invention are usually derivatives of 1,2-propylene oxide or both 1,2-propylene oxide and ethylene oxide, the ethylene oxide amounting to up to about 30 percent by weight of the propylene oxide and ethylene oxide. When ethylene oxide is used, the ethylene oxide residues can be present as blocks or can be alternatively or randomly distributed. In the manufacture of the polyether polyol, the propylene oxide or both propylene oxide and ethylene oxide are reacted with a polyhydric initiator, such as glycerol, trimethylethane, trimethylolpropane, or 1,2,6-hexanetriol.

Some representative polyether polyols which are useful in the practice of this invention are:

Dow Chemical Voranol 3140 or CP-3140 (a proprietary polyether polyol having an average molecular weight of about 3800 and a hydroxyl number of about 45); Olin PG-412 (a proprietary polyether triol having an average molecular weight of about 3500 and an average hydroxyl number of about 48); Jefferson Chemical F-3514 (a proprietary propoxylated glycerol having an average molecular weight of about 3500 and a hydroxyl number of about 48); Dow Voranol 2310 (a proprietary polyether polyol having a hydroxyl number of between about 55.1 and 57.8, a percent hydroxyl of between about 1.67 and 1.75, a pH in a solution of 1 part water to and 10 parts methanol between about 7.2 and 8.8, and an acid number of about 0.03 mg maximum): Dow Voranol 2100 (a proprietary polyether polyol having a hydroxyl number between about 55.4 and 57.1, a percent hydroxyl between about 1.68 and 1.73, a pH in a solution of 1 part water to 10 parts methanol between about 7.2 and 8.8, and an acid number of about 0.03 mg maximum); Dow Voranol 2120 (a proprietary polyether polyol having a hydroxyl number between about 54.8 and 57.4, a percent hydroxyl between about 1.66 and 1.74, a pH in a solution of 1 part water to 10 parts methanol of between about 7.7 and 8.8, and an acid number of about 0.03 mg maximum); and Dow XD-1421 (a proprietary polyether polyol having a hydroxyl number of between about 54.8 and 57.4, an acid number of about 0.03 mg maximum, and a pH in a solution of 1 part water to 10 parts methanol between about 7.7 and 8.8).

In general, the normally liquid polyether polyol used in accordance with this invention will have an average molecular weight within the range from about 300 to about 20,000 and a hydroxyl number within the range from about 28 to 690.

Typical polyester polyols used in the practice of this invention include:

Jefferson Chemical F-50 (a polyester polyol prepared from diethylene glycol, trimethylol-propane and adipic acid, having an average molecular weight of about 2000 and a hydroxyl number of about 52; and Rucoflex R-302 (a proprietary highly branched, low molecular weight polyester polyol, having a hydroxyl number of about 400±20, a nominal hydroxyl equivalent weight of about 140, a nominal molecular weight of about 700, a nominal functionality of about 5.0, a viscosity in cps at 60° C. of about 1900 as measured by a Brookfield viscometer LVF and at 23° C. of about 38,000, an acid number of about 1.5 mg. maximum and a specific gravity 20/20° C. of about 1.16.

Other polyester polyols within this invention include the Formrez polyester polyols from Witco Chemical such as: Formrez F15-22 (a propretary polyester polyol having a 2000 molecular weight linear poly (diethylene adipate), a hydroxyl number of about 55, an acid number of about 1.0 mg maximum, and a viscosity of about 7000 cps at 25° C.); Formrez F18-62 (a proprietary polyester polyol having a 1000 molecular weight linear poly (diethylene adipate), a hydroxyl number of about 112, an acid number of about 1.0 mg. maximum, and a viscosity of about 1800 cps at 25° C.); Formrez L12-17 (a proprietary polyester polyol having a 500 molecular weight linear poly (diethylene adipate), a hydroxyl number of about 225, an acid number of about 1.0 mg maximum, and a viscosity of about 500 cps at 25° C.); Formrez F7-37 (a proprietary polyester polyol having a 2000 molecular weight linear poly (ethylene adipate), a hydroxyl number of about 56, and an acid number of about 0.5 mg maximum); Formrez F10-13 (a proprietary polyester polyol having a 1000 molecular weight linear poly (ethylene adipate), a hydroxyl number of about 110, and an acid number of about 0.5 mg maximum); Formrez F10-37 (a proprietary polyester polyol having a 2000 molecular weight linear poly (ethylene adipate), a hydroxyl number of about 56, and an acid number of about 0.5 mg maximum); Formrez F7-67 (a proprietary polyester polyol having a 2000 molecular weight linear poly (propylene adipate), a hydroxyl number of about 58, an acid number of about 0.8 mg maximum, and a viscosity of about 12,000 cps at 25° C.); Formrez L8-71 (a proprietary polyester polyol having a 2000 molecular weight linear poly (ethylene/propylene adipate), a hydroxyl number of about 59, and an acid number of about 0.8 mg maximum); Formrez F10-91 (a proprietary polyester polyol having a 1000 molecular weight linear poly (ethylene/propylene adipate), a hydroxyl number of about 113, and an acid number of about 0.3 mg maximum); Formrez F9-30 (a proprietary polyester polyol having a 2000 molecular weight linear poly (1,4-butane adipate), a hydroxyl number of about 55, and an acid number of about 0.5 mg maximum); Formrez F13-35 (a proprietary polyester polyol having a 1000 molecular weight linear poly (1,4-butane adipate), a hydroxyl number of about 111, and an acid number of about 0.8 mg maximum); Formrez F20-30 (a proprietary polyester polyol having a 2000 molecular weight linear poly (neopentyl adipate), a hydroxyl number of about 58, and an acid number of about 0.8 mg maximum); Formrez L4-67 (a proprietary polyester polyol having a 2000 molecular weight linear poly (1,6-hexane adipate), a hydroxyl number of about 55, and an acid number of about 0.5 mg maximum); Formrez L5-55 (a proprietary polyester polyol having a 1000 molecular weight linear poly (1,6-hexane adipate), a hydroxyl number of about 110, and an acid number of about 0.8 mg maximum).

In general, the normally liquid polyester polyols used in accordance with this invention will have an average molecular weight within the range from about 600 to about 40,000 and a hydroxyl number within the range from about 28 to 690.

Although the applicant does not wish to be bound by any particular theory, it is believed that the enzyme is protected from degradation by a physical adsorption and a chemical bonding of the carboxyl groups of the enzyme with the hydroxyl group of the polyol. When thus bound, the enzyme is preserved from the physical and chemical changes inherent in enzyme degradation. When placed in wash water with a detergent, the water insoluble polyol is not affected by the water, but is released upon exposure to higher temperature water and other conditions, such as changes in the wash water pH and solution agitation, which break the emulsion and release the enzyme.

The polyol, being water insoluble, requires the use of a non-aqueous solvent and a surfactant to solubilize it and promote the reaction between the hydroxyl groups of the polyol and the carboxyl groups of the enzyme which are believed to provide for enzyme stabilization.

The solvents which can be used in accordance with the teachings of this invention include aliphatic and aromatic hydrocarbon solvents. These include paraffinic hydrocarbons having a boiling range of from about 35 to 251° C., isoparaffinic hydrocarbons having a boiling range of from about 35° to 251° C., low odor petroleum solvents having a boiling rage of from about 35° to 251° C., aromatic solvents, kerosene, d-limonene, pine oil, and mixtures thereof.

Suitable hydrocarbon solvents also include isoparaffinic hydrocarbons, including mixed $C_{10}$-$C_{12}$ isoparaffinic hydrocarbons sold under the tradename Isopar by Exxon Chemicals, Houston, Texas. These isoparaffinic hydrocarbons are branched chain fully saturated hydrocarbons and are characterized by boiling range, and available in boiling ranges of from 98° C. to 210° C. In addition to the isoparaffinic hydrocarbons, low odor petroleum solvents having a boiling range of 195° C. to 250° C., such as kerosene and d-limonene also are acceptable. From an odor standpoint, the isoparaffinic hydrocarbons are preferred, as these materials are low odor. However, if odor is not a consideration, substantially any of the above solvents can be utilized.

The aromatic solvents include xylene and toluene. If desired, methanol, ethanol, propanol and isopropyl alcohol can be used in combination with the hydrocarbon solvents. If an aromatic solvent is used, it is usually used in combination with an aliphatic hydrocarbon solvent, and preferably at a ratio of 5 parts aliphatic hydrocarbon solvent to 1 part aromatic solvent.

For a variety of reasons, it is preferred to utilize certain relatively high boiling point hydrocarbon solvents so that the solvent remains in contact for some time with the stain and so that the flammability of any product formulated is somewhat reduced. It is preferred to use an isoparaffinic hydrocarbon solvent having a boiling range from 157° C. to 210° C., and most preferably from 176° C. to 188° C.

The solvents utilized in the composition of the present invention can be present in an amount from 5 to 70% by weight and preferably from 5 to 45% by weight, and most preferably from 5 to 30% by weight. It is most preferable that since solvents are relatively expensive and a petroleum resource, that a minimum amount of solvent be utilized in the composition of the present invention, while at the same time maintaining stain removal.

The solvent serves the dual function of solubilizing oil-borne stains on the substrate to be cleaned and solubilizing the water insoluble polyol components in the formulation for ease of emulsification.

Optionally, oxidizing agents may be added to the above formula to improve cleaning. For example, pinane hydroperoxide with naphthenic acid salts may be added to obtain superior oil removal on polyester fabrics. These oxidizing agents are used in conventional amounts in formulations of this invention.

The method of preparing this water-in-oil emulsion prespotting laundry composition involves mixing the water insoluble polyester or polyester polyol with the enzyme, solvent and nonionic ethoxylated surfactant and separately blending the builder salt in an aqueous base carrier and then adding this blend to the above mixture with moderate agitation. The result is a water-in-oil emulsion composition.

This formula can be packaged as liquids in bottles or in pump dispensers. Alternatively, the formula of the present invention can be charged in an aerosol-type pressure package with a suitable propellent. Pressure packaging can be accomplished by charging aerosol cans by standard techniques with about 5 to 25% by weight of the composition of hydrocarbon liquid propellents such as propane, butane, isobultane, and the like, and mixtures thereof.

The prespotter compositions prepared in accordance with the teachings of this invention generally have a pH in the range of about 5 to 9, with a pH of about 6 to 8 being preferred.

Certain preferred embodiments are further illustrated in the following examples.

EXAMPLE #1

| Ingredients | Amount |
|---|---|
| Ethoxylated $C_{14}$–$C_{15}$ alcohol [7 Eto] (Neodol 45-7)[1] | 5.00 |
| Ethoxylated $C_{14}$–$C_{15}$ alcohol [1 Eto] (Neodol 45-1) | 5.00 |
| Polyester polyol (Rucoflex R-302 | 1.00 |
| Isoparaffinic solvent (Isopar K) | 30.00 |
| Protease enzyme (Esperase 80L from Novo) | 0.50 |
| Perfume (K5442 Florasynth) | 0.13 |
| Preservative (Kathon 866 from Rohm & Haas) | 0.05 |
| Tripotassium EDTA (50% active) | 4.85 |
| Citric acid (50% active) | 2.45 |

-continued

EXAMPLE #1

| Ingredients | Amount |
|---|---|
| Ammonia (30% conc.) | 0.44 |
| Calcium formate | 0.50 |
| Deionized water | balance |

[1]Eto is ethylene oxide.

The formula of Example 1 is effective in removing grass and blood stains, and is particularly effective in the removal of motor oil, chocolate, mustard, spaghetti and sebum.

EXAMPLE #2

| Ingredients | Amount |
|---|---|
| Nonylphenol ethoxylate [6 Eto] (Surfonic N-60)[2] | 6.00 |
| Nonylphenol ethoxylate [3 Eto] (Surfonic N-30)[2] | 0.50 |
| Polyether polyol (Dow XD-1421) | 1.00 |
| Isoparaffinic solvent (Isopar K) | 30.00 |
| Protease enzyme (Esperase 80L from Novo) | 0.50 |
| Perfume K5442 (Florasynth) | 0.13 |
| Preservative (Kathon 886 from Rohm & Hass) | 0.05 |
| Trisodium EDTA (50% active) | 4.85 |
| Citric acid (50% active) | 2.45 |
| Ammonium (30% conc.) | 0.44 |
| Sodium formate | 0.80 |
| Deionized water | balance |

[2]From Texaco

The formula of Example 2 is particularly useful in the effective removal of motor oil stains, and is also effective in the removal of grass and blood stains.

EXAMPLE #3

| Ingredients | Amount |
|---|---|
| Octylphenol ethoxylate [3.6 Eto] (Triton X-15)[3] | 2.00 |
| Octylphenol ethoxylate [7.8 Eto] (Triton X-35)[3] | 6.00 |
| Polyester polyol (Rucoflex R-302) | 1.00 |
| Isoparaffinic solvent (Isopar K) | 30.00 |
| Protease enzyme (Esperase 80L from Novo) | 0.50 |
| Perfume K5442 (Florasynth) | 0.13 |
| Preservative (Kathon 866 from Rohm & Haas) | 0.05 |
| Tripotassium NTA (50% active) | 4.85 |
| Citric acid (50% active) | 2.45 |
| Ammonia (30% conc.) | 0.44 |
| Calcium formate | 0.50 |
| Deionized water | balance |

[3]From Rohm & Haas.

The formula of Example 3 is particularly effective in removing stains from mustard, spaghetti and chocolate.

EXAMPLE #4

| Ingredients | Amount |
|---|---|
| Ethoxylated $C_{11}$–$C_{15}$ secondary alcohols [5 Eto] (Tergitol 15-S-5) | 3.00 |
| Ethoxylated $C_{11}$–$C_{15}$ secondary alcohols [7 Eto] (Tergitol 15-S-7) | 7.00 |
| Polyester polyol (Rucoflex R-302) | 1.00 |
| Isoparaffinic solvent (Isopar K) | 22.00 |
| Paraffinic solvent (deodorized kerosene) | 5.00 |
| Xylene | 3.00 |
| Amylase enzyme (American Enzyme Amylase) | 0.10 |
| Protease enzyme (Esperase 80L from Novo) | 0.30 |
| Lipase enzyme (American Enzyme Lipase) | 0.10 |
| Perfume K5442 (Florasynth) | 0.13 |
| Preservative (Kathon 866 from Rohm & Haas) | 0.05 |

-continued

| EXAMPLE #4 | |
|---|---|
| Ingredients | Amount |
| Sodium gluconate | 8.00 |
| Calcium formate | 0.50 |
| Deionized water | balance |

The formula of Example 4 is particularly effective in removal of stains from grape juice, gravy and cooking oils.

What is claimed is:

1. An improved water-in-oil prespotter laundry composition comprising:
   (a) from about 0.1 to 1% by weight of at least one enzyme;
   (b) from about 5 to 30% by weight of at least one ethoxylated nonionic surfactant;
   (c) from about 0.2 to 5% by weight of at least one of a water insoluble polyester polyol having a hydroxyl number from about 28 to 690 or a water insoluble polyether polyol having a hydroxyl number from about 28 to 690;
   (d) from about 0.1 to 10% by weight of at least one builder salt;
   (e) from about 5 to 70% by weight of at least one hydrocarbon solvent; and
   (f) the balance water; and having a pH in the range from about 5 to 9.

2. The composition of claim 1, wherein said ethoxylated nonionic surfactant is selected from the group consisting of ethoxylated aliphatic alcohols, ethoxylated alkylphenols, and mixtures thereof.

3. The composition of claim 2, wherein said ethoxylated nonionic surfactant is selected from the group consisting of primary or secondary alcohol ethoxylates having a carbon length of 8 to 22 carbon atoms and containing from 1 to about 100 moles of ethylene oxide per mole of alcohol; alkylphenol polyglycol ethers having a carbon length of 6 to 18 carbon atoms and containing from 1 to about 50 moles of ethylene oxide per mole of phenol, and mixtures thereof.

4. The composition of claim 1, wherein the enzyme is selected from the group consisting of proteases, lipases, amylases, and mixtures thereof.

5. The composition of claim 1, wherein the builder salt is selected from the group consisting of citrates, gluconates, borates, silicates, phosphates, chlorides, bicarbonates, carbonates, acetates, polyphosphates, phosphates, maleates, fumerates, formates and mixtures thereof.

6. The composition of claim 1, wherein the builder salt is selected from the group consisting of water soluble alkali metal salts of nitrilotriacetic acid and ethylene diamine tetracetic acid.

7. The composition of claim 1, wherein the hydrocarbon solvent is selected from the group consisting of paraffinic hydrocarbons having a boiling range of from about 35° to 251° C., isoparaffinic hydrocarbons having a boiling range of from about 35° to 251° C., low odor petroleum solvents having a boiling range of from about 35° to 251° C., aromatic solvents, kerosene, d-limonene, pine oil, and mixtures thereof.

8. A method for producing an improved water-in-oil prespotter laundry composition having a pH in the range from about 5 to 9 comprising the steps of:
   (1) mixing:
      (a) from about 0.1 to 1% by weight of at least one enzyme;
      (b) from about 5 to 30% by weight of at least one ethoxylated nonionic surfactant;
      (c) from about 0.2 to 5% by weight of at least one of a water insoluble polyester polyol having a hydroxyl number from about 28 to 690 or a water insoluble polyether polyol having a hydroxyl number from about 28 to 690; and
      (d) from about 5 to 70% by weight of at least one hydrocarbon solvent;
   (2) blending from about 0.1 to 10% by weight of at least one builder salt in an aqueous carrier; and
   (3) adding the mixture of (1) to the blend of (2).

9. The method of claim 8, wherein said ethoxylated nonionic surfactant is selected from the group consisting of ethoxylated aliphatic alcohols, ethoxylated alkylphenols, and mixtures thereof.

10. The method of claim 9, wherein said ethoxylated nonionic surfactant is selected from the group consisting of primary or secondary alcohol ethoxylates having a carbon length of 8 to 22 carbon atoms and containing from 1 to about 100 moles of ethylene oxide per mole of alcohol; alkylphenol polyglycol ethers having a carbon length of 6 to 18 carbon atoms and containing from 1 to about 50 moles of ethylene oxide per mole of alkylphenol, and mixtures thereof.

11. The method of claim 8, wherein the enzyme is selected from the group consisting of proteases, lipases, amylases, and mixtures thereof.

12. The method of claim 8, wherein the builder salt is selected from the group consisting of citrates, gluconates, borates, silicates, phosphates, chloride, bicarbonates, carbonates, acetates, polyphosphates, phosphates, maleates, fumerates, formates and mixtures thereof.

13. The method of claim 8, wherein the builder salt is selected from the group consisting of water soluble alkali metal salts of nitrilotriacetic acid and ethylene diamine tetracetic acid.

14. The method of claim 8, wherein the hydrocarbon solvent is selected from the group consisting of paraffinic hydrocarbons having a boiling range of from about 35° to 251° C., isoparaffinic hydrocarbons having a boiling range of from about 35° to 251° C., low odor petroleum solvents having a boiling range of from about 35° to 251° C., aromatic solvents, kerosene, d-limonene, pine oil, and mixtures thereof.

* * * * *